(12) United States Patent
Spataro et al.

(10) Patent No.: US 12,403,286 B2
(45) Date of Patent: Sep. 2, 2025

(54) PASSIVE DILATION IN CATHETER INSERTION SYSTEMS

(71) Applicant: Bard Access Systems, Inc., Salt Lake City, UT (US)

(72) Inventors: Joe Spataro, Cottonwood Heights, UT (US); Daniel B. Blanchard, Bountiful, UT (US); Kyle G. Thornley, Farmington, UT (US); Austin J. Mckinnon, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 0 days.

(21) Appl. No.: 17/542,096

(22) Filed: Dec. 3, 2021

(65) Prior Publication Data

US 2022/0176081 A1 Jun. 9, 2022

Related U.S. Application Data

(60) Provisional application No. 63/121,761, filed on Dec. 4, 2020.

(51) Int. Cl.
*A61M 25/00* (2006.01)
*A61M 25/06* (2006.01)

(52) U.S. Cl.
CPC .... *A61M 25/0662* (2013.01); *A61M 25/0068* (2013.01); *A61M 25/0082* (2013.01); *A61M 2025/0687* (2013.01)

(58) Field of Classification Search
CPC .............. A61M 25/0662; A61M 25/02; A61M 25/0023; A61M 25/0068; A61M 25/0082;
(Continued)

(56) References Cited

U.S. PATENT DOCUMENTS 2,566,499 A 9/1951 Richter
2,842,133 A 7/1958 Uhma
(Continued)

FOREIGN PATENT DOCUMENTS

CN 2456639 Y 10/2001
CN 210844555 U 6/2020
(Continued)

OTHER PUBLICATIONS

PCT/US2021/059256 filed Nov. 12, 2021 International Search Report and Written Opinion dated Mar. 23, 2022.
(Continued)

*Primary Examiner* — Laura A Bouchelle
*Assistant Examiner* — Sarah Dympna Grasmeder
(74) *Attorney, Agent, or Firm* — Rutan & Tucker LLP (57) ABSTRACT

Disclosed herein is a catheter, which in some embodiments includes a distal section configured to enter a skin insertion site. The distal section can include a tapered junction having one or more dilation structures configured to dilate the skin insertion site. The distal section can further include a distal portion extending from a distal end of the tapered junction, the distal portion having a diameter smaller than a proximal portion of the catheter. In combination, the tapered junction, the one or more dilation structures, and the specific actions of the user urging the catheter into the insertion site can result in an improved fit of the catheter in the insertion site.

8 Claims, 7 Drawing Sheets

(58) Field of Classification Search
CPC .. A61M 2025/0687; A61M 2025/0286; A61M 2025/0293; A61M 2025/0096; A61B 17/32093; A61B 17/3415; A61B 17/3209; A61B 2017/3458; A61B 90/02
See application file for complete search history.

(56) References Cited

U.S. PATENT DOCUMENTS

| | | | |
|---|---|---|---|
| 3,921,631 A * | 11/1975 | Thompson | A61M 25/065 604/508 |
| 4,601,710 A | 7/1986 | Moll | |
| 4,693,250 A | 9/1987 | Coons | |
| 4,889,112 A | 12/1989 | Schachner et al. | |
| 4,955,890 A | 9/1990 | Yamamoto et al. | |
| 5,279,285 A | 1/1994 | Griggs | |
| 5,334,157 A | 8/1994 | Klein et al. | |
| 5,509,900 A * | 4/1996 | Kirkman | A61M 25/04 606/198 |
| 5,755,697 A | 5/1998 | Jones et al. | |
| 5,800,450 A | 9/1998 | Lary et al. | |
| 5,843,115 A | 12/1998 | Morejon | |
| 6,033,388 A | 3/2000 | Nordstrom et al. | |
| 6,517,519 B1 | 2/2003 | Rosen et al. | |
| 6,761,725 B1 | 7/2004 | Grayzel et al. | |
| 9,114,227 B2 | 8/2015 | Blanchard | |
| 9,480,498 B1 | 11/2016 | Kessler | |
| 10,028,762 B1 | 7/2018 | Slupchynskyj | |
| 10,376,675 B2 | 8/2019 | Mitchell et al. | |
| 2002/0040231 A1 | 4/2002 | Wysoki | |
| 2004/0133227 A1 | 7/2004 | Shang et al. | |
| 2004/0181246 A1 | 9/2004 | Heppler | |
| 2004/0181273 A1 | 9/2004 | Brasington et al. | |
| 2005/0177183 A1 | 8/2005 | Thorne et al. | |
| 2009/0024089 A1 | 1/2009 | Levine et al. | |
| 2009/0076435 A1 | 3/2009 | Melsheimer et al. | |
| 2009/0125030 A1 | 5/2009 | Tebbe et al. | |
| 2010/0057056 A1 | 3/2010 | Gurtner et al. | |
| 2012/0130417 A1 | 5/2012 | Lepulu et al. | |
| 2012/0226299 A1 | 9/2012 | Heppler | |
| 2013/0197558 A1 | 8/2013 | Ingold, Jr. et al. | |
| 2016/0128713 A1 | 5/2016 | Rauchwerger et al. | |
| 2016/0346503 A1* | 12/2016 | Jackson | A61M 25/0021 |
| 2017/0128700 A1* | 5/2017 | Roche Rebollo | A61M 25/0105 |
| 2017/0296792 A1 | 10/2017 | Ornelas Vargas et al. | |
| 2019/0307485 A1* | 10/2019 | Kiev | A61B 17/3496 |
| 2019/0351183 A1 | 11/2019 | Ishida | |
| 2020/0061322 A1 | 2/2020 | De Rezende Neto | |
| 2020/0086095 A1* | 3/2020 | Kleinhaus | A61B 17/3478 |
| 2020/0155190 A1 | 5/2020 | Basadonna et al. | |
| 2020/0222077 A1 | 7/2020 | Takahashi | |
| 2020/0246597 A1 | 8/2020 | Broniec et al. | |
| 2021/0069471 A1 | 3/2021 | Howell | |
| 2021/0085927 A1 | 3/2021 | Howell | |
| 2021/0106351 A1 | 4/2021 | Hossack et al. | |
| 2021/0113809 A1 | 4/2021 | Howell | |
| 2021/0113810 A1 | 4/2021 | Howell | |
| 2021/0121661 A1 | 4/2021 | Howell | |
| 2021/0212722 A1 | 7/2021 | Kiev et al. | |
| 2022/0152368 A1 | 5/2022 | Thornley et al. | |
| 2023/0141739 A1 | 5/2023 | Doctor et al. | |
| 2023/0233227 A1 | 7/2023 | Lindekugel et al. | |
| 2023/0241353 A1 | 8/2023 | Howell et al. | |
| 2023/0241354 A1 | 8/2023 | Howell | |
| 2023/0255660 A1 | 8/2023 | Howell | |
| 2023/0255661 A1 | 8/2023 | Howell | |
| 2023/0277212 A1 | 9/2023 | Howell | |
| 2023/0277813 A1 | 9/2023 | Howell | |
| 2023/0277814 A1 | 9/2023 | Howell | |

FOREIGN PATENT DOCUMENTS

| | | |
|---|---|---|
| CN | 111481303 A | 8/2020 |
| CN | 112155683 A | 1/2021 |
| DE | 10100332 A1 | 7/2002 |
| DE | 202004012605 U1 | 10/2004 |
| WO | 9108709 A1 | 6/1991 |
| WO | 9412091 A1 | 6/1994 |
| WO | 02087666 A2 | 11/2002 |
| WO | 03022129 A2 | 3/2003 |
| WO | 2011024013 A1 | 3/2011 |
| WO | 2011057282 A2 | 5/2011 |
| WO | 2012087506 A2 | 6/2012 |
| WO | 2016176065 A1 | 11/2016 |
| WO | 2017006323 A1 | 1/2017 |
| WO | 2020076691 A1 | 4/2020 |
| WO | 2022104149 A1 | 5/2022 |
| WO | 2022120201 A1 | 6/2022 |
| WO | 2023081465 A1 | 5/2023 |
| WO | 2023122313 A1 | 6/2023 |
| WO | 2023141170 A1 | 7/2023 |
| WO | 2023150263 A1 | 8/2023 |
| WO | 2023150314 A1 | 8/2023 |
| WO | 2023158643 A1 | 8/2023 |
| WO | 2023158645 A1 | 8/2023 |
| WO | 2023167943 A1 | 9/2023 |
| WO | 2023168005 A1 | 9/2023 |
| WO | 2023168097 A1 | 9/2023 |

OTHER PUBLICATIONS

Rauchwerger, Jacob Jeffrey, Michael Serle, and Jeffrey C. Astbury. "Novel Wire-Guided Scalpel to Facilitate Central Venous Catheter Insertion without a Skin Bridge." Vascular Specialist International 37 (2021).
PCT/US2021/061857 filed Dec. 3, 2021 International Search Report and Written Opinion dated Apr. 11, 2022.
PCT/US2022/049134 filed Nov. 7, 2022 International Search Report and Written Opinion dated Mar. 30, 2023.
PCT/US2022/053889 filed Dec. 22, 2022 International Search Report and Written Opinion dated Apr. 20, 2023.
PCT/US2023/011067 filed Jan. 18, 2023 International Search Report and Written Opinion dated May 11, 2023.
PCT/US2023/012270 filed Feb. 3, 2023 International Search Report and Written Opinion dated Jun. 21, 2023.
PCT/US2023/012345 filed Feb. 3, 2023 International Search Report and Written Opinion dated Jun. 27, 2023.
PCT/US2023/013056 filed Feb. 14, 2023 International Search Report and Written Opinion dated Jun. 12, 2023.
PCT/US2023/013058 filed Jun. 7, 2023 International Search Report and Written Opinion dated Jun. 7, 2023.
PCT/US2023/014298 filed Mar. 1, 2023 International Search Report and Written Opinion dated Jun. 1, 2023.
PCT/US2023/014384 filed Mar. 2, 2023 International Search Report and Written Opinion dated Jun. 16, 2023.
PCT/US2023/014532 filed Mar. 3, 2023 International Search Report and Written Opinion dated Jul. 10, 2023.
U.S. Appl. No. 17/525,774, filed Nov. 12, 2021 Non-Final Office Action dated Jan. 24, 2024.
U.S. Appl. No. 17/525,774, filed Nov. 12, 2021 Advisory Action dated Aug. 26, 2024.
U.S. Appl. No. 17/525,774, filed Nov. 12, 2021 Final Office Action dated Jun. 18, 2024.
U.S. Appl. No. 17/525,774, filed Nov. 12, 2021 Non-Final Office Action dated Jan. 28, 2025.
U.S. Appl. No. 18/098,607, filed Jan. 18, 2023 Non-Final Office Action dated Feb. 6, 2025.

* cited by examiner

PASSIVE DILATION IN CATHETER INSERTION SYSTEMS

PRIORITY

This application claims the benefit of priority to U.S. Provisional Application No. 63/121,761, filed Dec. 4, 2020, which is incorporated by reference in its entirety into this application.

BACKGROUND

In some catheter placement procedures, dilation of the tissue surrounding an insertion site is a core activity that occurs during catheter placement. Proper dilation of the tissue allows an improved fit of the catheter. Current dilation techniques are done by hand, using a separate hardened component and/or a skin nick to relieve the tension in the skin while dilating the tissue. These techniques require the insertion and removal of various instruments adding complexity, time and increasing the risk of infection. Furthermore, these techniques may lead to undesired tissue deflection and require increased pushing forces resulting in over dilation of the tissue surrounding the insertion site. It would be beneficial to be able to dilate only the tissue necessary for the fit of the catheter and reduce the necessity of the skin nick. Disclosed herein is a system and method of use that address the foregoing.

SUMMARY

Disclosed herein is a distal section of a catheter configured to enter a skin insertion site including a tapered junction including one or more dilation structures configured to dilate the skin insertion site, and a distal portion extending from a distal end of the tapered junction, the distal portion having a diameter smaller than a proximal portion of the catheter.

In some embodiments, the one or more dilation structures includes one or more protrusions or a helix extending from a side wall of the tapered junction.

In some embodiments, the one or more dilation structures extend radially from the side wall of the tapered junction.

In some embodiments, each protrusion includes a proximal edge and a distal edge.

In some embodiments, each protrusion extends longitudinally from the proximal edge to the distal edge.

In some embodiments, each protrusion extends laterally from the side wall to an apex.

In some embodiments, the apex is located between a longitudinal mid-point and one of the proximal edge or the distal edge, including the proximal edge or the distal edge.

In some embodiments, each protrusion defines a proximal face extending between the apex and the proximal edge.

In some embodiments, each protrusion defines a distal face extending between the apex and the distal edge.

In some embodiments, the proximal face defines a cutting edge extending longitudinally through a midline of the proximal face.

In some embodiments, the distal face defines a cutting edge extending longitudinally through a midline of the distal face.

In some embodiments, the protrusions are longitudinally organized into a first line of two or more protrusions and a second line of two or more protrusions disposed on opposite sides of the tapered junction.

In some embodiments, the proximal face and the distal face of each protrusion coordinate to define a rounded outer profile.

In some embodiments, each protrusion of the first line is longitudinally aligned with each protrusion of the second line.

In some embodiments, each protrusion of the first line is longitudinally offset from each protrusion of the second line.

In some embodiments, the helix includes a right handed helix or a left handed helix.

In some embodiments, the helix includes beveled or chamfered edges.

Also disclosed herein is a method of inserting a catheter including inserting a distal section of a catheter into a skin insertion site, the distal section having a tapered junction including one or more dilation structures configured to dilate the skin insertion site and a distal portion extending from a distal end of the tapered junction, the distal portion having a diameter smaller than a proximal portion of the catheter, dilating the skin insertion site, and advancing the proximal portion of the catheter into the skin insertion site.

In some embodiments, the one or more dilation structures include one or more protrusions or a helix extending from a side wall of the tapered junction.

In some embodiments, each protrusion includes a proximal face and a distal face.

In some embodiments, the proximal face defines a cutting edge extending longitudinally through a midline of the proximal face.

In some embodiments, the distal face defines a cutting edge extending longitudinally through a midline of the distal face.

In some embodiments, dilating the skin insertion site includes using the cutting edge to dilate the insertion site.

In some embodiments, dilating the skin insertion site includes rotating a helical dilation structure about a longitudinal axis to dilate the insertion site.

In some embodiments, wherein the helix includes a right handed helix or left handed helix.

In some embodiments, the helix includes beveled or chamfered edges.

In some embodiments, dilating the skin insertion site includes using the beveled or chamfered edges to dilate the insertion site.

In some embodiments, dilating the skin insertion site includes twisting the distal section of the catheter around a longitudinal axis, clockwise or counterclockwise.

In some embodiments, dilating the skin insertion site includes wiggling the distal section of the catheter about a transverse or lateral axis.

These and other features of the concepts provided herein will become more apparent to those of skill in the art in view of the accompanying drawings and following description, which describe particular embodiments of such concepts in greater detail.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

Figure 1:
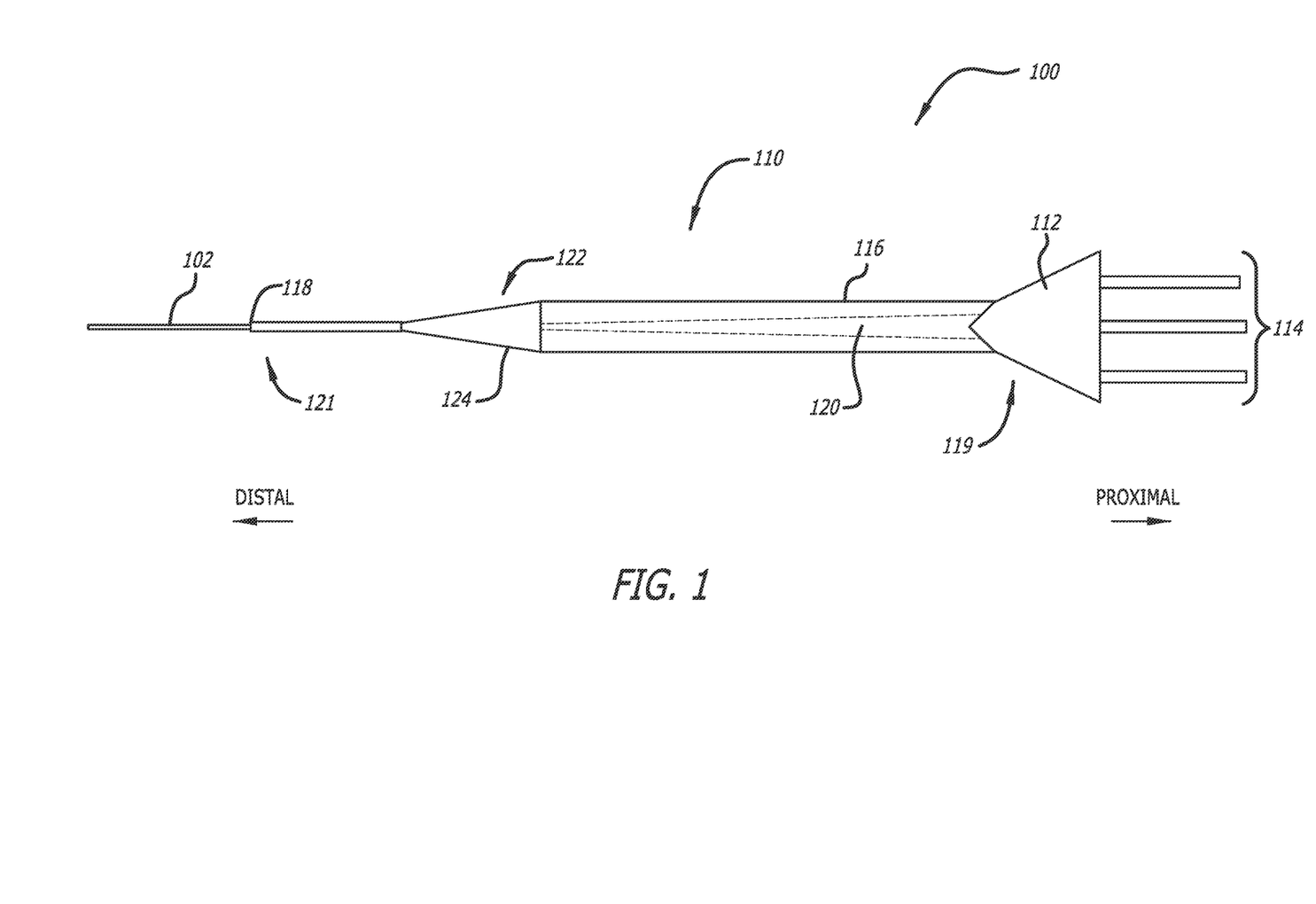
FIG. 1 illustrates a plan view of a catheter insertion system, in accordance with some embodiments.

FIG. 1 illustrates a plan view of a catheter insertion system 100, in accordance with some embodiments. In some embodiments, the catheter insertion system 100 includes a catheter 110 having a hub 112 disposed at a proximal end and including one or more extension legs 114 extending proximally from the proximal end of the hub 112. In some embodiments, the catheter 110 includes a catheter tube 116 distally extending from the distal end of the hub 112. In some embodiments, the catheter tube 116 may be configured to slide over a guidewire 102. The catheter tube 116 includes a proximal end 119 and a distal section 121 terminating in a distal tip 118 and can define one or more catheter lumens 120 therein. In some embodiments, the catheter 110 may include a Rapid Insertion Central Catheter ("RICC"), such as described, for example, in U.S. Pat. Nos. 10,376,675; 11,517,719; U.S. Publication No. 2021/0069471; U.S. Publication No. 2021/0113809; U.S. Publication No. 2021/0113810; and U.S. Publication No. 2021/0121661, each of which is incorporated by reference in its entirety into this application. As used herein, the catheter insertion system 100 can be used to place a RICC to access the vasculature of a patient. However, it will be appreciated that embodiments disclosed herein can be used to place various catheters, cannulas, single lumen catheters, multi-lumen catheters, intravenous (IV) catheters, peripheral intravenous line (PIV) catheters, peripherally inserted central catheters (PICC), central venous catheter (CVC), dialysis catheters, drainage catheters, and the like, without limitation.

Placing a catheter 110 requires dilating the tissue surrounding an insertion site since typically the insertion site is smaller than the diameter of the catheter 110. Current dilation techniques use a hardened component that can cause tissue deflection and excessive stretching of the skin tissue as the hardened component is forced through the insertion site. The less movement of the insertion site and the less tissue dilated around the insertion site can lead to a more accurate placement of the catheter 110 within the body and a better fit of the catheter 110 within the insertion site.

In some embodiments, a cross-sectional shape of the catheter tube 116 may be cylindrical, a triangular prism, a rectangular prism, or the like, although other cross-sectional shapes are also contemplated. In some embodiments, the catheter tube 116 may be configured to have a tapered junction 122 between the proximal end 119 of the catheter tube 116 and the distal section 121 of the catheter tube 116. In some embodiments, the tapered junction 122 may be configured to include one or more dilation structures 123 extending from a side wall 124 of the tapered junction 122 that will be described in more detail herein.

Figure 2:
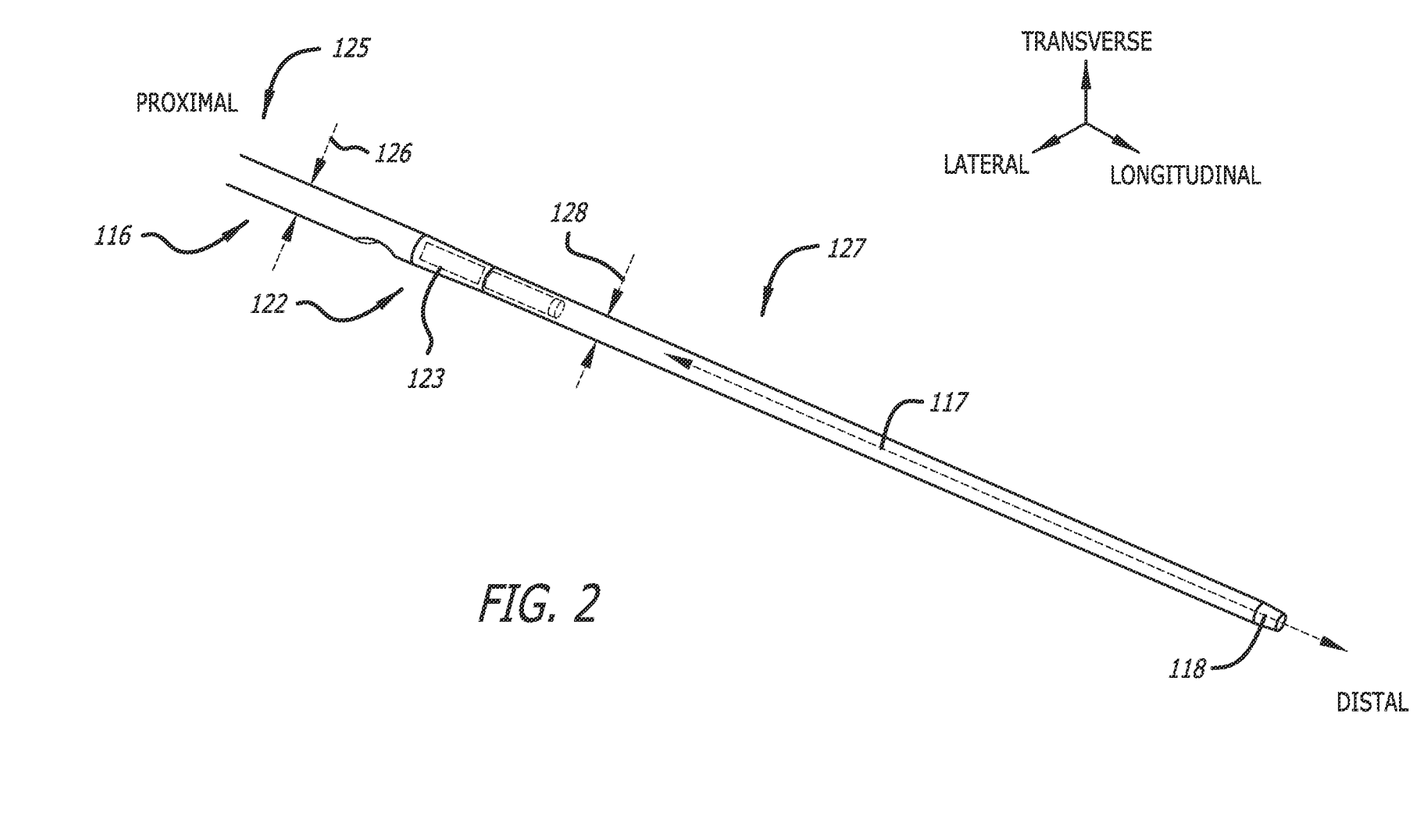
FIG. 2 illustrates a perspective view of components of a catheter insertion system including a tapered junction, in accordance with some embodiments.

FIG. 2 illustrates a perspective view of components of a catheter insertion system 100 including the tapered junction 122, in accordance with some embodiments. In some embodiments, the catheter tube 116 includes a proximal portion 125, the tapered junction 122 having the side wall 124 and a distal portion 127 distal the tapered junction 122. In some embodiments, the catheter tube 116 defines a central longitudinal axis 117. The proximal portion 125 has a second diameter 126 and the distal portion 127 has a first diameter 128. In some embodiments, the second diameter 126 is larger than the first diameter 128. The tapered junction 122 is a portion of the catheter tube 116 that is tapered from the proximal portion 125 to the distal portion 127 and from the second diameter 126 to the first diameter 128. In some embodiments, the tapered junction 122 may be evenly tapered, or unevenly tapered from the proximal portion 125 to the distal portion 127. In some embodiments, the first diameter 128 and the second diameter 126 may be associated with the French catheter scale. In some embodiments, the tapered junction 122 may be configured to include one or more dilation structures 123 that may be configured to have a specific shape to dilate the tissue surrounding an insertion site that will be described in more detail herein.

Figure 3A:
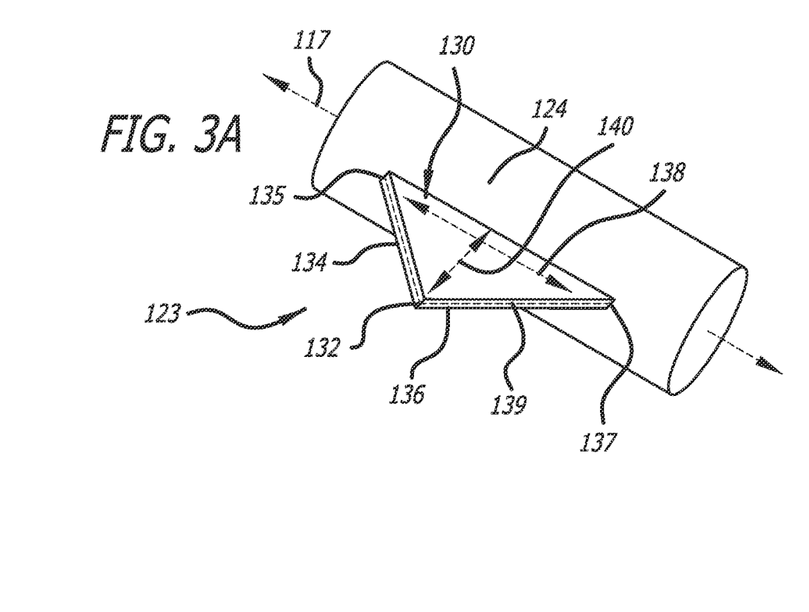
FIG. 3A illustrates a schematic view of an exemplary dilation structure, in accordance with some embodiments.
Figure 3B:
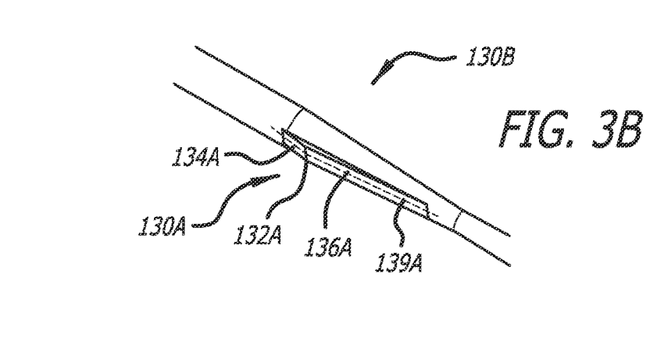
FIGS. 3B-3I illustrates perspective views of various embodiments of the one or more dilation structures, in accordance with some embodiments.
Figure 3C:
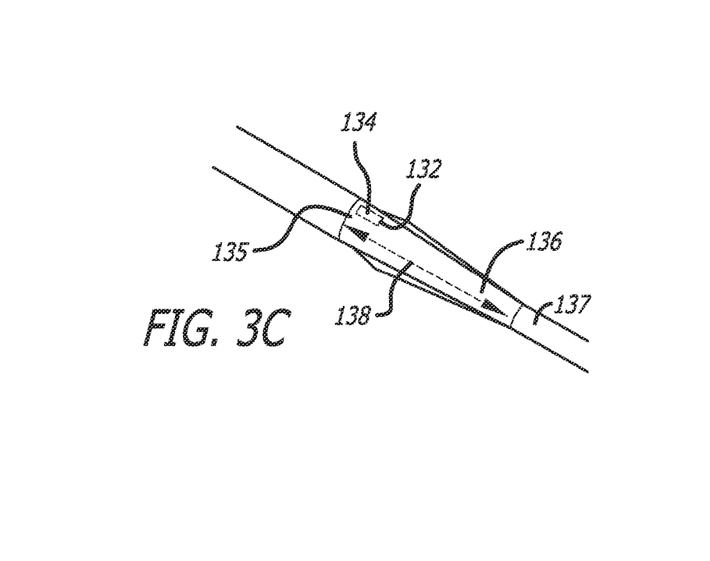
Figure 3D:
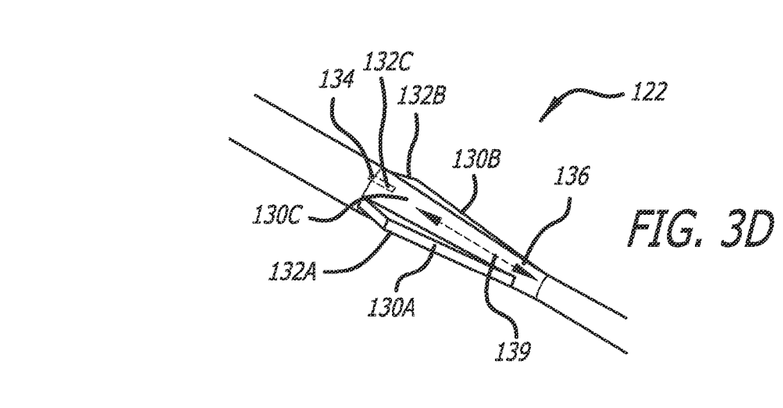

FIG. 3A illustrates a schematic view of an exemplary dilation structure, in accordance with some embodiments. In some embodiments, the one or more dilation structures 123 may be configured to include structures that extend from the tapered junction 122 that dilate tissues upon insertion of the catheter 110 into an insertion site. In some embodiments, the one or more dilation structures 123 include a protrusion 130 extending from the side wall 124. In some embodiments, the one or more dilation structures extend radially from the side wall 124 or longitudinally from a proximal edge 135 to a distal edge 137. In some embodiments, the protrusion 130 may be configured to extend from the side wall 124 to an apex 132. In some embodiments, the apex 132 defines the furthest point of the protrusion 130 from the side wall 124. In some embodiments, the protrusion 130 further defines a proximal face 134, extending laterally between the apex 132 and the proximal edge 135 and a distal face 136 extending between the apex 132 and the distal edge 137. In some embodiments, the protrusion 130 includes a length 138 and a width 140. In some embodiments, as illustrated in FIGS. 3C-3D, the length 138 may remain the same while the apex 132 may be disposed anywhere along the length 138 including a longitudinal mid-point, towards and including the proximal edge 135 or the distal edge 137.

In some embodiments, the one or more dilation structures 123 may include one or more protrusions 130 or helices 160 that will be described in more detail herein. FIGS. 3B-3I illustrate perspective views of various embodiments of the protrusions 130 or helices 160, in accordance with some embodiments. As will be appreciated, the protrusions 130 can extend radially from the side wall 124. In some embodiments, the one or more protrusions 130 can extend from the side wall 124 at a same distance or at a different distance from the side wall 124 of the tapered junction 122, as will be described in more detail herein. In some embodiments, as illustrated in FIGS. 3B-3C, the protrusion 130 can include various geometries. For example, as illustrated in FIG. 3B, the proximal face 134A or distal face 136A can define a cutting edge extending longitudinally through a midline 139 of the proximal face 134A or the distal face 136A. In some embodiments, the cutting edge may be configured to assist the user with dilating the tissue around the insertion site and avoid tissue deflection. As illustrated in FIG. 3D, the tapered junction 122 can include a plurality of protrusions 130A-C, defining the longitudinally rounded distal face 136, the midline 139 and the longitudinally rounded proximal face 134. An apex 132A of a first protrusion 130A can be longitudinally offset from an apex 132B of a second protrusion 130B.

Figures 3E, 3F, 3G, 3H, 3I:
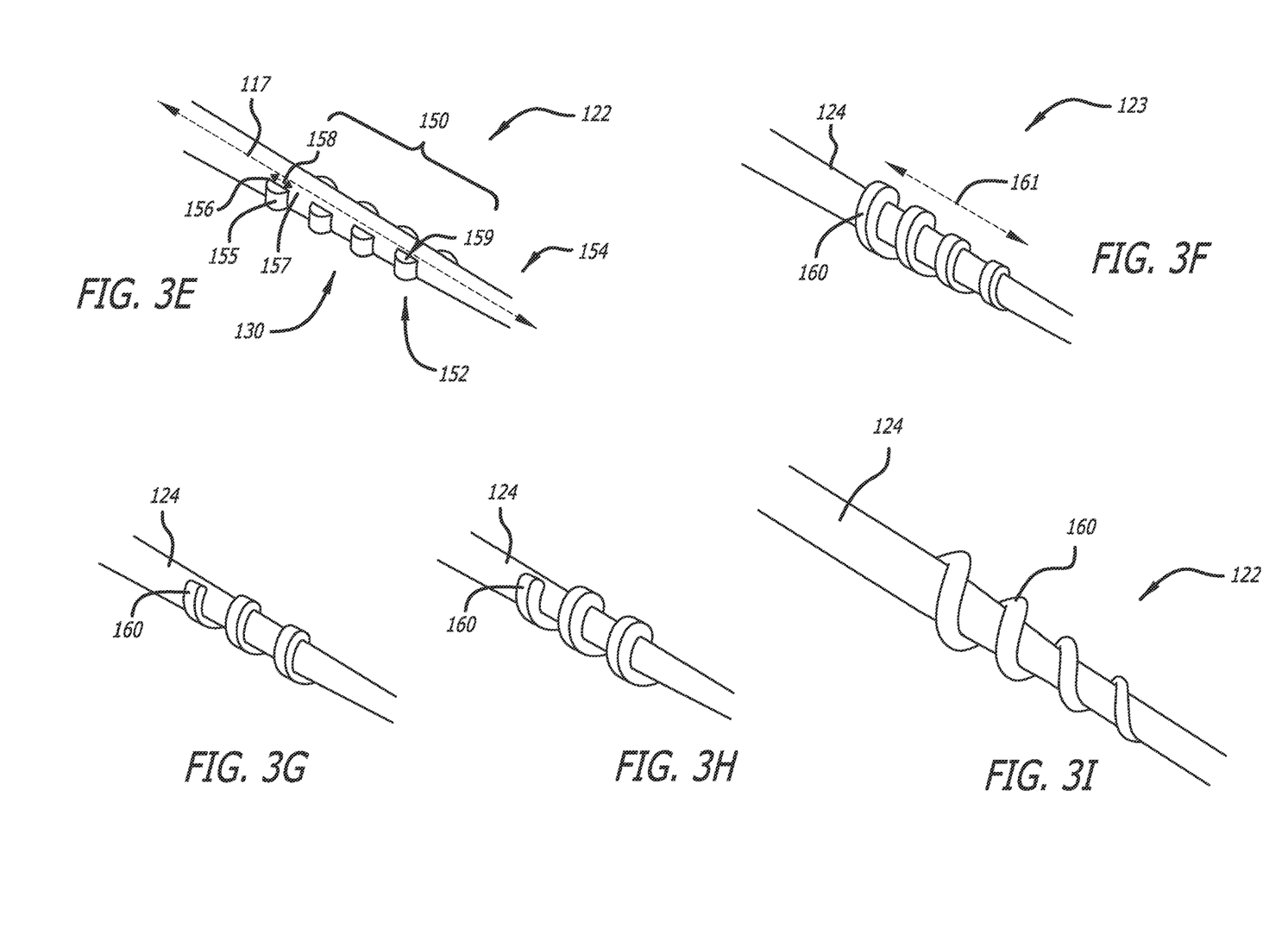

FIG. 3E illustrates a perspective view of the one or more protrusions 130 wherein the one or more protrusions 130 include a plurality of ribs 150, wherein the plurality of ribs 150 are repeated rounded protrusions. In some embodiments, each rib of the plurality of ribs 150 includes a rib face 155 extending from a proximal edge 156 to a distal edge 157, a rib length 158 extending from the proximal edge 156 to the distal edge 157, and a rib width 159. In some embodiments, the rib face 155 defines the rounded outer profile of the protrusion 130. In some embodiments, the rib length 158 of the plurality of ribs 150 may be the same or varied. In some embodiments, the rib width 159 of the plurality of ribs 150 may be the same or varied. In an embodiment, the rib width 159 tapers from a larger rib width 159 proximally to a smaller rib width 159 distally.

In some embodiments, the plurality of ribs 150 may be randomly distributed or evenly distributed on the side wall 124 of the tapered junction 122. In some embodiments, the plurality of ribs 150 may be longitudinally organized into a first line 152 of two or more ribs and a second line 154 of two or more ribs. In an embodiment, each rib in the first line 152 may be longitudinally aligned with each rib in the second line 154. In an embodiment as illustrated in FIG. 3E, each rib in the first line 152 may be longitudinally offset from each rib in the second line 154. Each rib in the first line 152 may be evenly spaced or unevenly spaced from the other ribs in the first line 152 and each rib in the second line may be evenly spaced or unevenly spaced from the other ribs in the second line. The first line 152 and the second line 154 can be disposed on opposite sides of the tapered junction 122. In some embodiments, the first line 152 may be aligned along a lateral side and the second line 154 may be aligned along a transverse side, or at an angle therebetween.

In an embodiment, the first line of ribs 152 can be arranged in a helical pattern about the longitudinal axis 117, where each rib of the first line of ribs 152 are rotationally offset by an angle about the longitudinal axis 117 and longitudinally offset by a distance. In an embodiment, each rib of the first line of ribs 152 can be rotationally offset by the same angle or by different angles. In an embodiment, each rib of the first line of ribs 152 can be longitudinally offset by the same distance or different distances.

FIGS. 3F-3I illustrates a perspective view of the one or more dilation structures 123 wherein the dilation structure 123 includes the helix 160 extending radially about longitudinal axis 117 from the side wall 124. In some embodiments, the helix 160 may be a right handed helix or a left handed helix. In some embodiments, as illustrated in FIG. 3F, the helix 160 may have a longitudinal length 161. In some embodiments, e.g. FIG. 3F, the dilation structure 123 can include a relatively high number of revolutions per longitudinal length 161, providing a relatively "tighter" helical structure. In some embodiments, e.g. FIG. 3G, the dilation structure 123 can include a relatively low number of revolutions per longitudinal length 161, providing a relatively "looser" helical structure.

In some embodiments, each revolution of the helix 160 may extend radially the same distance from the side wall 124, as illustrated in FIG. 3G, or each revolution may extend different distances from the side wall 124. For example, as illustrated in FIG. 3H, the helix 160 may extend a greater distance from the side wall 124 at a proximal end and may extend a lesser distance from the side wall 124 at a distal end. Advantageously, by rotating the tapered junction 122, including the helical dilation structure 123, the mechanical action of the helix 160 pulls the tapered junction 122 through the insertion site 104, avoiding tissue deflection or distortion. In some embodiments, as illustrated in FIG. 3I, the helix 160 may be configured to have beveled, chamfered, squared or rounded edges. The beveled or chamfered edges may be configured to partially cut or fully cut the tissue surrounding the insertion site 104 as the helix 160 is rotated, further dilating the tissue. Although FIGS. 3A-3I illustrate various embodiments of the one or more dilation structures 123 of the tapered junction 122, other shapes or protrusions are considered.

FIGS. 4A-4D illustrate cross sections of the one or more dilation structures 123 including the one or more protrusions 130 of the tapered junction 122, in accordance with some embodiments. In some embodiments, the catheter tube 116 includes the one or more lumens 120 extending therethrough. In some embodiments, the protrusions 130 include a height 141. As used herein, the "height" of the protrusion 130 is a distance of an outer most point of the protrusion 130 extending radially from the side wall 124. In some embodiments, the protrusion 130 defines a width 140. As used herein a "width" is a distance extending parallel to the side wall 124. In some embodiments, the protrusions 130 may have the same width 140 and the same height 141 or different widths 140 and different heights 141.

Figure 4A:
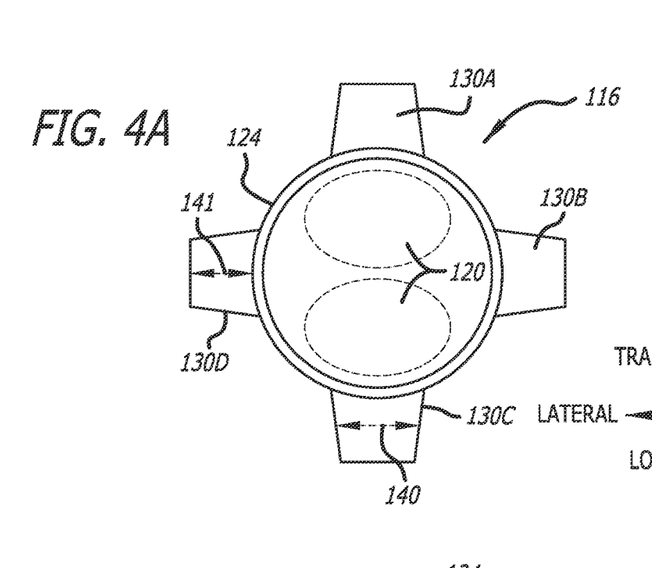
FIGS. 4A-4D illustrate cross sectional views of various embodiments of the dilation structures, in accordance with some embodiments.
Figure 4B:
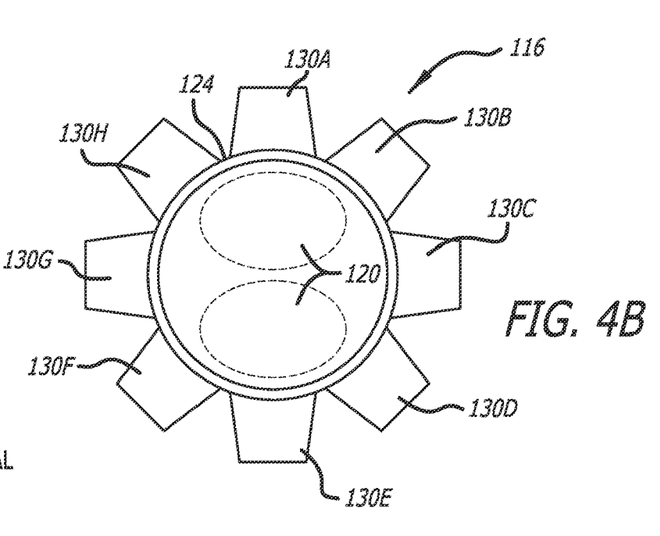

As illustrated in FIG. 4A, the tapered junction 122 may include four protrusions 130A-D extending radially from the side wall 124 of the tapered junction 122. In some embodiments, a first ridge 130A may be equidistant from a second ridge 130B and a fourth ridge 130D. In some embodiments, the fourth ridge 130D may be equidistant from the first ridge 130A and a third ridge 130C. Simply put, the four protrusions 130A-D may be evenly spaced radially around the tapered junction 122. As illustrated in FIG. 4B, in some embodiments, the tapered junction 122 may include eight ridges 130A-H extending from the side wall 124 of the tapered junction 122. In some embodiments, the eight ridges 132A-H may be even spaced, unevenly spaced or clustered together around the tapered junction 122. Although eight ridges are illustrated, greater or lesser number of ridges are also contemplated.

Figure 4C:
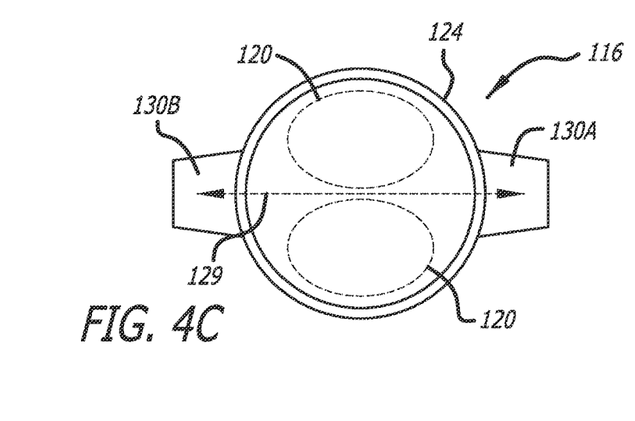
Figure 4D:
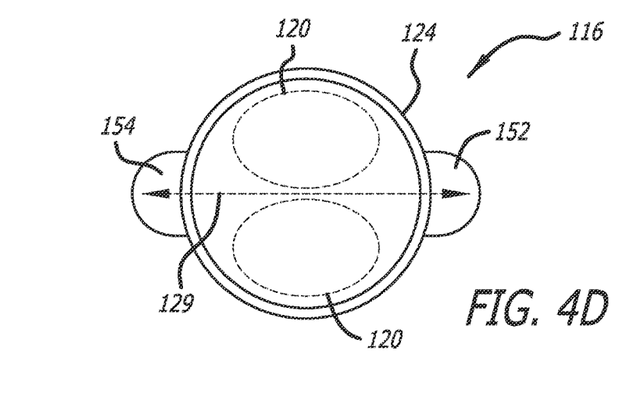

As illustrated in FIG. 4C, in some embodiments, the tapered junction 122 may include two protrusions 130A, 130B extending from the side wall 124 of the catheter tube 116. In some embodiments, the first protrusion 130A and the second protrusion 130B define a lateral axis 129. In some embodiments, the first protrusion 130A may be longitudinally aligned with the second protrusion 130B, defining a lateral axis 129 on opposite sides of the tapered junction 122. In some embodiments, the first protrusion 130A may be longitudinally offset from the second protrusion 130B. In some embodiments, the one or more protrusions 130 may include the plurality of ribs 150. In some embodiments, the plurality of ribs 150 may be organized in the first line 152 and the second line 154. As illustrated in FIG. 4D, in some embodiments, the first line 152 may longitudinally aligned with the second line 154, on opposite sides of the catheter tube 116. In some embodiments, the first line 152 may be longitudinally offset from the second line 154. In some embodiments, the plurality of ribs 150 may radially extend evenly or unevenly from the side wall 124 to define different distances from the side wall 124 of the tapered junction 122. In some embodiments, the plurality of ribs 150 located proximally may radially extend a greater distance from the side wall 124 than the ribs located distally. In some embodiments, the plurality of ribs 150 may be organized into a plurality of lines, evenly spaced around the tapered junction 122. In some embodiments, the plurality of ribs 150 may be spaced in an organized configuration or a random configuration around the catheter tube 116. In some embodiments the plurality of ribs may be arranged in a helical line about the longitudinal axis 117.

Figure 5A:
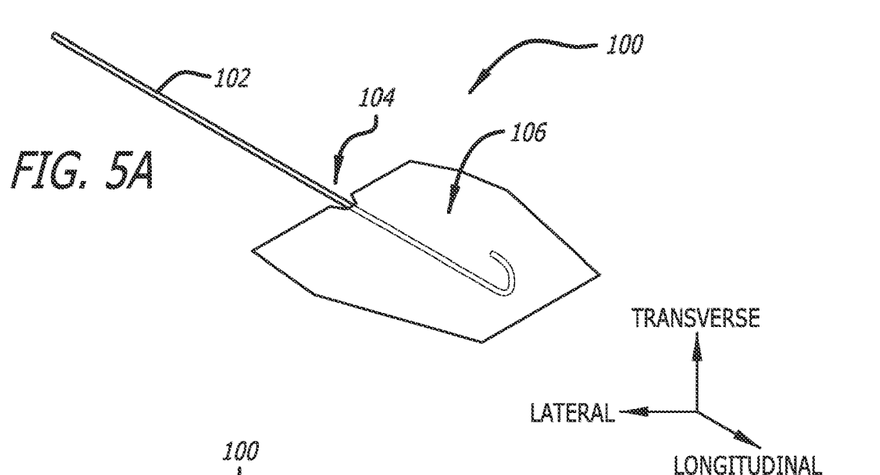
FIGS. 5A-5C illustrate an exemplary method of inserting a catheter into an insertion site, in accordance with some embodiments.
Figure 5B:
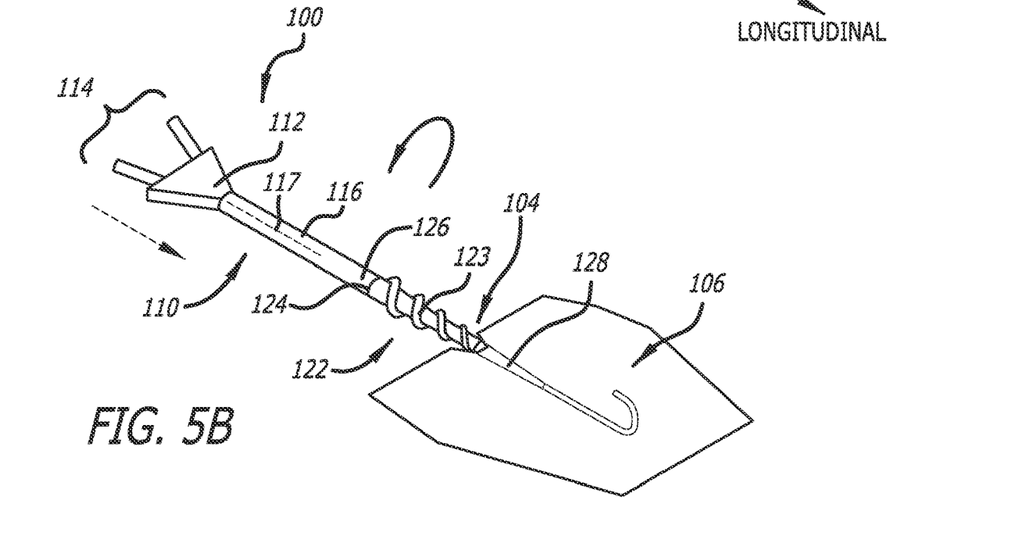
Figure 5C:
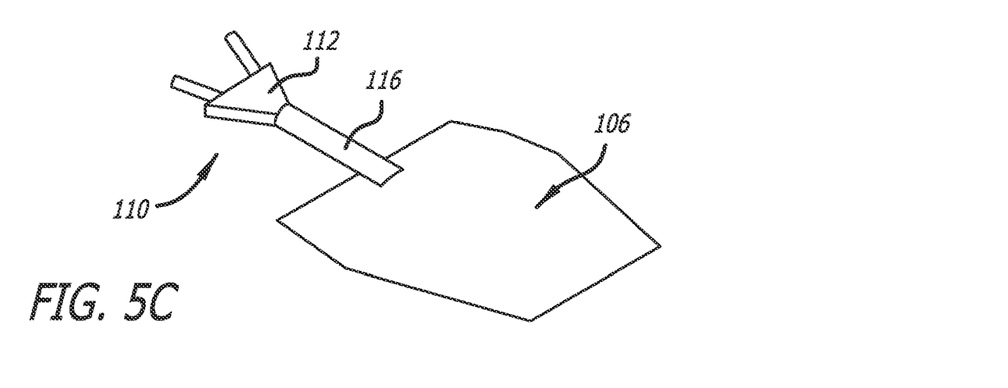

FIGS. 5A-5C illustrate an exemplary method of using inserting a catheter 110 into an insertion site 104. In some embodiments, the catheter insertion system 100 includes a guidewire 102. As illustrated in FIG. 5A, the guidewire 102 may be inserted into an insertion site 104 in a target area 106. In some embodiments, the target area 106 may include a target vessel. In some embodiments, a user may confirm the guidewire 102 is in the correct target location. In some embodiments, as illustrated in FIG. 5B, the catheter insertion system 100 further includes the catheter 110 having the hub 112 disposed at a proximal end and including one or more extension legs 114 extending proximally from the proximal end of the hub 112. The catheter 110 includes the catheter tube 116 distally extending from the distal end of the hub 112. The catheter tube 116 may be configured to slide over the guidewire 102. The catheter tube 116 includes the proximal end 119 and a distal section 121, terminating in the distal tip 118 and can define the one or more catheter lumens 120 therein. The catheter tube 116 further includes the proximal portion 125, the tapered junction 122 having the side wall 124 and the distal portion 127. The proximal portion 125 has the second diameter 126 and the distal portion 127 has the first diameter 128 with the second diameter 126 being larger than the first diameter 128. The tapered junction 122 may be configured to include one or more dilation structures 123 radially extending from the side wall 124 and configured to have a specific shape to dilate the tissue surrounding the skin insertion site 104 while mitigating tissue deflection. The dilation structures 123 can include one or more protrusions 130 or helices 160.

Once the guidewire 102 is placed at the correct target location, the catheter 110 may be slid over the guidewire 102 and urged into the skin insertion site 104 as illustrated in FIG. 5B. Since the distal portion 127 defines a smaller first diameter 128, the distal portion 127 can enter the skin insertion site 104 more easily. The tapered junction 122 including the one or more dilation structures 123 can then dilate the skin insertion site 104 for the larger second diameter 126 and the proximal portion 125. As the catheter 110 is urged into the skin insertion site 104, the one or more dilation structures 123 facilitates dilating the tissue around the skin insertion site 104 by stretching the tissue around the skin insertion site 104 along a lateral axis. For example, a rotating helix 160 may be configured to use mechanical advantage to pull the tapered junction 122 through the skin insertion site 104, minimizing tissue deflection. In some embodiments, the user may further twist the catheter 110 clockwise or counterclockwise about the longitudinal axis 117 while urging the catheter 110 into the skin insertion site 104 to further dilate the tissue surrounding the insertion site 104.

In some embodiments, the user may "wiggle" the catheter 110 back and forth along the lateral axis, transverse axis or a combination thereof, while urging the catheter 110 into the insertion site 104 to further dilate the tissue surrounding the insertion site 104. In some embodiments, e.g. FIG. 3D, the user may wiggle the catheter 110 back and forth along the lateral or a transverse axis. In some embodiments, e.g. FIGS. 3E-3I, the user may wiggle and twist the catheter 110 while urging the catheter 110 into the insertion site 104. In some embodiments, the user may continue to wiggle or twist the catheter 110 until the catheter 110 is completely inserted into the insertion site 104, as illustrated in FIG. 5C. Once the catheter 110 is fully inserted, the user may confirm proper target location placement of the catheter 110 through imaging. In some embodiments, using the catheter 110 to dilate the insertion site 104 leads to an increased fit of the catheter 110 into the insertion site 104, while minimizing tissue deflection around the insertion site 104.

Figure 6:
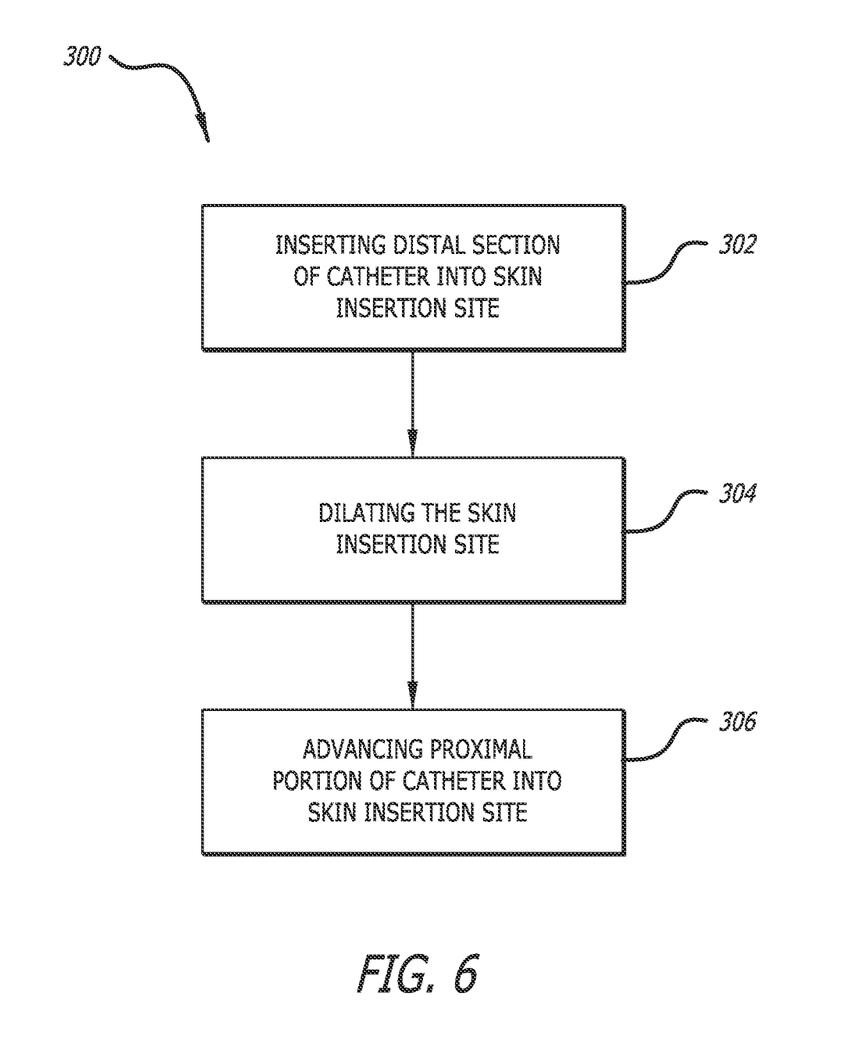
FIG. 6 illustrates a flow chart of an exemplary method of inserting a catheter, in accordance with some embodiments.

FIG. 6 illustrates a flow chart of an exemplary method 300 of inserting a catheter 110 into an insertion site 104 using a catheter insertion system 100, in accordance with some embodiments. In some embodiments, the method 300 includes inserting a distal section 121 of the catheter 110 into the insertion site 104 (block 302). In some embodiments, the distal section 121 includes the tapered junction 122 having one or more dilation structures 123 radially extending from the side wall 124 and a distal portion 127 extending from the distal end of the tapered junction, having the first diameter 128.

The method 300 includes dilating the skin insertion site 104 (block 304). In some embodiments, dilating the insertion site 104 includes dilating from the smaller first diameter 128 to the larger second diameter 126. In some embodiments, dilating the skin insertion site 104 includes urging the tapered junction 122 of the catheter 110 into the skin insertion site 104, the tapered junction 122 includes the one or more dilation structures 123 radially extending from the side wall 124. In some embodiments, the one or more dilation structures 123 include the one or more protrusions 130 or the helix 160. In some embodiments, dilating the insertion site 104 includes twisting the catheter 110 clockwise or counterclockwise around the central longitudinal axis 117. In some embodiments, dilating the insertion site 104 includes wiggling the catheter 110 along the transverse or lateral axis.

The method 300 further includes advancing the proximal portion 125 of the catheter 110 into the insertion site 104 (block 306). In some embodiments, the proximal portion 125 includes the second diameter 126. In some embodiments, the second diameter 126 is greater than the first diameter 128.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A catheter configured to enter a skin insertion site, comprising:
    a hub disposed proximally and including one or more extension legs extending proximally therefrom;
    a catheter tube extending distally from the hub and defining a first catheter lumen and a second catheter lumen, each of which are in fluid communication with an extension leg of the one or more extension legs;
    a tapered junction coupled to a distal end of the catheter tube and including a dilation structure configured to dilate the skin insertion site, the dilation structure comprising:
        a first protrusion extending along a longitudinal axis between a first distal edge and a first proximal edge and extending along a lateral axis to a first apex, the first apex disposed proximate a first mid-point between the first distal edge and the first proximal edge, the first protrusion including a first cutting edge; and
        a second protrusion extending along the longitudinal axis between a second distal edge and a second proximal edge and extending along the lateral axis to a second apex, the second apex disposed proximate a second mid-point between the second distal edge and the second proximal edge, the second protrusion including a second cutting edge; and
    a distal portion extending from a distal end of the tapered junction, the distal portion having a diameter smaller than a diameter of a proximal portion of the catheter tube and defining a distal part of the first catheter lumen, the second catheter lumen terminating at an aperture disposed in a side wall and disposed adjacent the distal end of the catheter tube.

2. The catheter according to claim 1, wherein an outermost lateral diameter extending between the first apex and the second apex, is greater than, the diameter of the catheter tube.

3. The catheter according to claim 2, wherein an outermost transverse diameter of the dilation structure, extending perpendicular to the lateral axis is less than the diameter of the catheter tube.

4. The catheter according to claim 1, wherein the first protrusion defines a first proximal face extending between the first apex and the first proximal edge, and the second protrusion defines a second proximal face extending between the second apex and the second proximal edge.

5. The catheter according to claim 4, wherein the first protrusion defines a first distal face extending between the first apex and the first distal edge, and the second protrusion defines a second distal face extending between the second apex and the second distal edge.

6. The catheter according to claim 4, wherein the first proximal face defines the first cutting edge extending longitudinally through a first midline of the first proximal face, and the second proximal face defines the second cutting edge extending longitudinally through a second midline of the second proximal face.

7. The catheter according to claim 5, wherein the first distal face defines the first cutting edge extending longitudinally through a first midline of the first distal face, and the second distal face defines the second cutting edge extending longitudinally through a second midline of the second distal face.

8. The catheter according to claim 1, wherein the tapered junction, the distal portion and the distal end of the catheter tube are configured to be placed subcutaneously through the skin insertion site.

* * * * *